(12) United States Patent
Hoogenraad et al.

(10) Patent No.: US 6,230,045 B1
(45) Date of Patent: May 8, 2001

(54) APPARATUS AND METHOD FOR LOCALIZING AN OBJECT IN A TURBID MEDIUM

(75) Inventors: Johannes H. Hoogenraad, Houten; Jeroen C. J. Paasschens; Gert W. 't Hooft, both of Eindhoven, all of (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/197,310

(22) Filed: Nov. 20, 1998

(30) Foreign Application Priority Data

Nov. 22, 1997 (EP) .................................................. 97203659

(51) Int. Cl.$^7$ ...................................................... A61B 6/00
(52) U.S. Cl. .......................... 600/473; 600/476; 356/432; 250/341.1
(58) Field of Search ..................................... 600/310, 473, 600/476; 356/432–435; 250/339.06, 339.09, 339.12, 341.1, 338.1

(56) References Cited

U.S. PATENT DOCUMENTS

| | | | |
|---|---|---|---|
| 5,899,865 | * 5/1999 | Chance | 600/473 |
| 5,907,406 | * 5/1999 | Papaioannou et al. | 356/432 |
| 5,941,827 | * 8/1999 | Papaioannou | 600/473 |
| 5,983,121 | * 11/1999 | Tsuchiya | 600/310 |

OTHER PUBLICATIONS

"The forward and inverse problems in time resolved infrared imaging", by S.R. Arridge, as published in Medical Optical Tomography, vol. IS11, 1993.

* cited by examiner

*Primary Examiner*—Ruth S. Smith
(74) *Attorney, Agent, or Firm*—John F. Vodopia

(57) ABSTRACT

The invention relates to a method of localizing an object in a turbid medium. The invention also relates to a device for carrying out such a method. The method can be used in optical mammography during which a part of a breast of a female body is examined by means of light. To this end, the part of the breast is introduced into a holder of the device, said holder being provided with light sources and detectors. In order to realize an optical coupling between the light sources and the detectors and the breast, a calibration medium is introduced. After measurement of the intensities for a plurality of light paths between the light sources and the detectors, the measured intensity is normalized. In order to counteract artifacts which are caused by deviations of the optical properties of the calibration medium and the mean optical properties of the part of the breast, according to the invention the measured intensities are corrected prior to the reconstruction of the interior of the breast. The corrected intensity for a light path to be selected between a light source and a detector is determined by a combination of a normalized intensity of the selected light path, the normalized intensities, lengths of the light paths, and a length of the selected light path.

10 Claims, 3 Drawing Sheets

APPARATUS AND METHOD FOR LOCALIZING AN OBJECT IN A TURBID MEDIUM

BACKGROUND OF THE INVENTION

1. Field of the Invention

The invention relates to a method of localizing an object in a turbid medium, which method includes the following steps: immersing the turbid medium in a calibration medium, irradiating the turbid medium, measuring intensities of a part of the light transported through the turbid medium and the calibration medium along a plurality of light paths, normalizing the measured intensities and reconstructing an image of the interior of the turbid medium from the normalized intensities. The invention also relates to a device for carrying out a method of this kind.

2. Description of the Related Art

In the context of the present application the term light is to be understood to mean electromagnetic radiation of a wavelength in the range of from 400 to 1400 nm. Furthermore, a turbid medium is to be understood to mean a substance consisting of a material having a high light scattering coefficient. Examples in this respect are an Intralipid solution or biological tissue. Furthermore, attenuation coefficient is to be understood to mean the inverse diffuse absorption distance K which is given as, $K=\sqrt{3\mu_a\mu'_s}$ in which $\mu'_s$ is the reduced scatter coefficient and $\mu_a$ is the absorption coefficient.

A method of this kind is described in patent application EP 97202187.7. The known method can be used for in vivo breast examinations to determine the presence of tumors in breast tissue of a human or animal female. In order to counteract edge effects, according to the known method an attenuation coefficient of the calibration medium is made equal to a predetermined mean attenuation coefficient of the breast tissue. This can be achieved, for example by choosing a calibration medium in the form of a liquid with a solution of, for example Intralipid, having an attenuation coefficient which is equal to the predetermined mean attenuation coefficient of the breast tissue. Another possibility is to add a dye to the liquid with the dissolved Intralipid with a predetermined fixed percentage, and to detune the wavelength of the light to be generated by the light source in such a manner that the attenuation coefficient of the calibration medium is equal to the predetermined mean attenuation coefficient of the breast tissue. Furthermore, in order to prevent artefacts in the reconstructed image which are due to transitions between the calibration medium and an environment of the calibration medium, the measured intensities are normalized.

It is a drawback of the known method that an actual mean attenuation coefficient of the breast tissue of the body to be examined varies relative to the predetermined mean attenuation coefficient. This is due, for example to the fact that a mean attenuation coefficient of breast tissue of a group of females of approximately the same age is taken for the value of the predetermined mean attenuation coefficient. Consequently, artifacts are liable to occur in the reconstructed image of the interior of the breast.

SUMMARY OF THE INVENTION

It is an object of the method according to the invention to counteract said artifacts in the reconstructed image. To this end, the method according to the invention is characterized in that it includes a step for performing a correction on the normalized intensities in which a corrected intensity of a light path to be selected is determined by a combination of the normalized intensity of the selected light path, the normalized intensities, lengths of the light paths and a length of the selected light path. As a result of the use of the corrected intensities in the reconstruction of the image, artifacts caused by mismatching of the attenuation coefficient of the calibration medium and the actual mean attenuation coefficient of the turbid medium are counteracted. The invention is based on the recognition of the fact that in an infinite medium for a first order approximation for a selected light path having a length r and an intensity $I_{ijk}$ a first attenuation coefficient $K_1$ of a calibration medium can be recalculated to an intensity $I_{ref}$ associated with a second attenuation coefficient $K_2$ of the reference medium. Furthermore, if the intensities for a given $K_1$ of a calibration medium are known, source strengths and photodetector sensitivities are also defined, so that artefacts in the reconstructed image which are caused by a change of the intensity of a light source to be used or by a change of the sensitivity of a photodetector are counteracted. Furthermore, it is assumed that edge effects which occur between the calibration medium and the turbid medium or the edge effects which occur between the calibration medium and a holder containing the calibration medium and the turbid medium will change in a predictable manner when the attenuation coefficient K of the calibration medium varies, so that the edge effects can be compensated after the reconstruction. A further advantage consists in that in order to perform the correction, a calibration measurement need be determined only once so as to determine the intensities associated with the light paths in the calibration medium. This calibration is subsequently used to determine the corrections of the normalized intensities for all subsequent measurements performed by means of the same device on different human or animal bodies by use of the formula $$\ln\left(\frac{I_{ref}}{I_{cal}}\right) = (K_2 - K_1)r \tag{1}$$

in which r is the length of a selected light path between a light source and a photodetector. As a result of the estimation of $K_2-K_1$ from the combination of the normalized intensities and lengths of the plurality of light paths, a corrected intensity can be determined for a light path to be selected by means of $I''=I'-(K_2-K_1)r$, in which I' represents the normalized intensity and r represents the length of the selected light path. Consequently, the results of intensity measurements of the object in the reference medium can be determined without performing a measurement of the object in the reference medium.

A special version of the method according to the invention is characterized in that a value of the combination comprises a function of the length of the selected light path and a derivative of the normalized intensity to the length of the light path. In conformity with the formula (1), it appears that the derivative constitutes an estimate of the difference $K_2-K_1$. The derivative is equal to a direction coefficient of a reference line representing the logarithm of the ratio of the measured intensity of the calibration medium to the measured intensity of the reference medium as a linear function $a_1 \cdot r$ of the selected light path, a first order parameter $a_1$ of which corresponds to an estimate of the difference $K_2-K_1$ between the attenuation coefficients of the calibration medium and the reference medium, respectively.

A further version of the method according to the invention is characterized in that the normalized intensity of a light path to be selected is determined by a logarithm of a ratio of a first intensity of a selected light path in the turbid medium and the calibration medium to a second intensity of the selected light path in the calibration medium. As a result of this normalization, the corrected intensity I" for a light path to be selected is determined from the measured intensity in conformity with the formula $$I'' = \ln\left(\frac{I_{measurement}}{I'_{cal}}\right) - a_1 \cdot r,$$

in which $I_{measurement}$ represents the measured intensity of the selected light path in the turbid medium and the calibration medium, $I_{cal}$ represents the measured intensity of the selected light path in the calibration medium, $a_1$ represents the direction coefficient of the reference line, and r represents the length of the selected light path.

By using a first constant b in the correction, a correction can be made for a change of a coupling-in efficiency of the light from the calibration medium into the turbid medium or for a change in the attenuation coefficient K due to a changing reduced scatter coefficient $\mu_{s1}$. Furthermore, the correction of a normalized intensity I" for a light path to be selected between a light source and a photodetector is determined by $$I'' = \ln\left(\frac{I_{measurement}}{I_{ref}}\right) = \ln\left(\frac{I_{measurement}}{I_{cal}}\right) - a_1 r - b$$

in which $I_{measurement}$ represents the measured intensity of the selected light path in the turbid medium and the calibration medium, $I_{cal}$ represents the measured intensity of the selected light path in the calibration medium, $a_1$ represents the direction coefficient of the reference line, r represents the length of the selected light path and b represents the first constant.

A further version of the method according to the invention is characterized in that the reconstructed image is corrected for the calibration medium by adding a second constant to attenuation coefficients of voxels of the turbid medium, which voxels correspond to pixels of the reconstructed image. An example of said second constant is the difference $a_1 = K_2 - K_1$ between the attenuation coefficients of the calibration medium and the reference medium, respectively.

The invention also relates to a device for localizing objects in turbid media which is characterized in that it includes correction means for performing a correction on the normalized intensities, a corrected intensity of a light path to be selected being determined by a combination of a normalized intensity of the selected light path, the normalized intensities, lengths of the light paths and a length of the selected light path.

BRIEF DESCRIPTION OF THE DRAWING

The above and other, more detailed aspects of the invention will be described in detail hereinafter, by way of example, with reference to the drawings. Therein.

DETAILED DESCRIPTION OF THE PREFERRED EMBODIMENT

Figure 1:
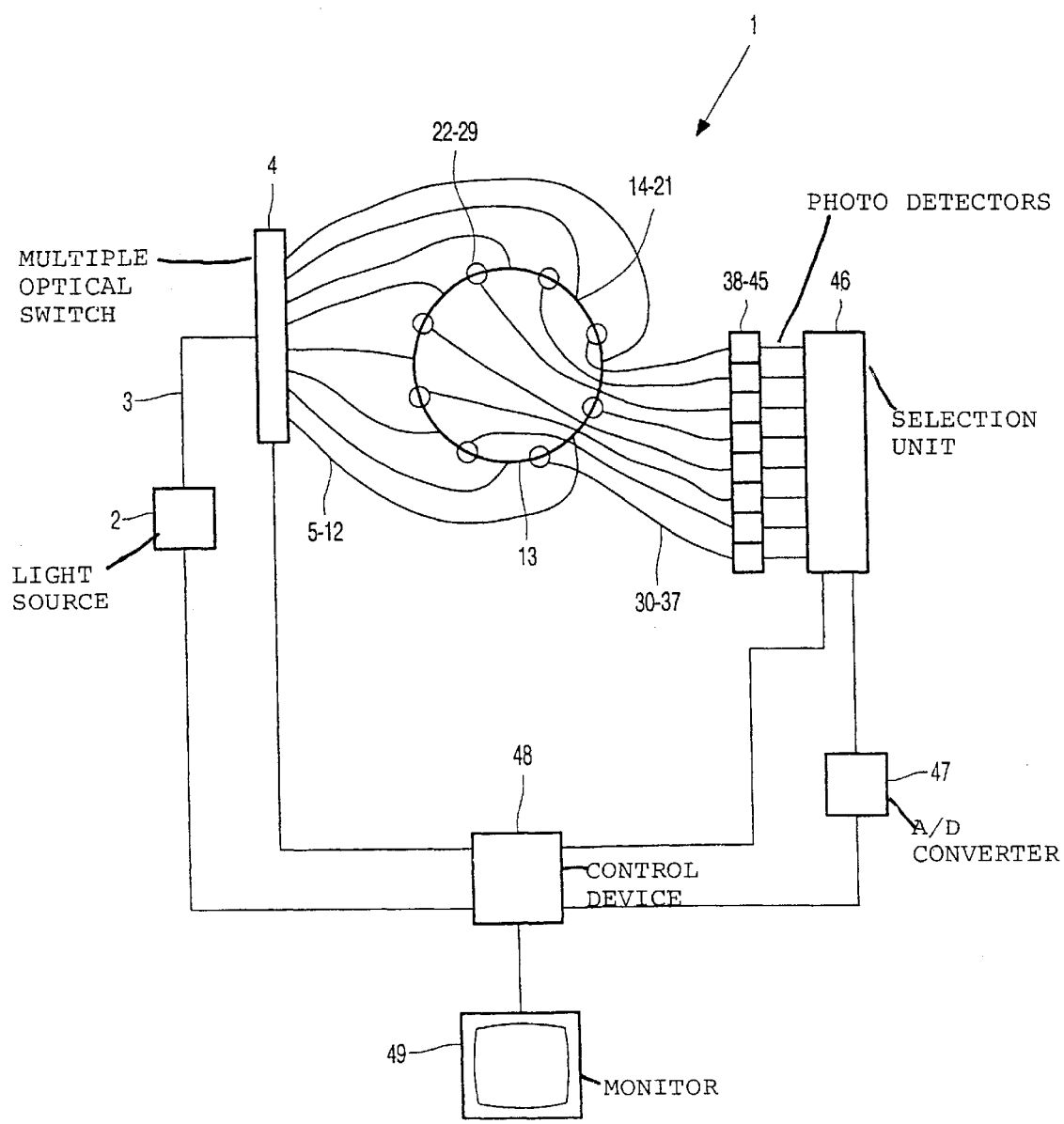
FIG. 1 shows a device for performing measurements on a turbid medium.

FIG. 1 shows an embodiment of a device according to the invention, being an optical mammography device 1 in the present case. Even though the device according to the invention is described, by way of example, as a mammography device, it can also be used for the examination of other parts of a human or animal body. The device described herein is intended for the in vivo localization of inhomogeneities in breast tissue of a part of a breast of a human body. A malignant tumor is an example of such an inhomogeneity. The device according to the invention is arranged to image such anomalies when they are still very small, so that a carcinoma can be detected at an early stage. However, detection takes place without exposing the patient to the risks of examination by means of ionizing radiation, for example X-rays.

The device 1 includes a first plurality of N measuring light sources 14–21, a second plurality of M photodetectors 38–45, and a holder 13. The measuring light sources are mounted in the wall of a holder 13 in positions $r_i$, where i=1 ... N. The M photodetectors 38–45 are optically coupled to photodetector openings 22–29 in positions $r_j$ in the holder 13, where j=1 ... M. The numbers N and M are fixed and are valued, for example between 64 and 256. In practice these numbers equal 256 for N as well as M. In FIG. 1 the number of measuring light sources 14–21 and the number of photodetector openings 22–29 are chosen to be equal to eight for the sake of simplicity. The device 1 also includes a light source 2, a first optical light conductor 3, a multiple optical switch 4 and the first plurality of second optical conductors 5–12. The multiple optical switch 4 connects the light source 2, via the first optical conductor 3 and a second optical conductor, to one of the light transmitting openings 14–21 in the wall of the holder 13, said openings constituting the measuring light sources. The light source 2 used is, for example a semiconductor laser with a wavelength of 810 nm. The measuring device 1 also includes a third plurality of optical conductors 30–37, a selection unit 46, an analog-to-digital converter 47 and a control device 48. The third optical conductors 30–37 are connected, via photodetector openings 22–29 in the wall of the holder 13, to the corresponding number of photodetectors 38–45. The exits of the photodetectors 38–45 are connected to the analog-to-digital converter 47 via the selection unit 46. The output of the analog-to-digital converter is connected to an input of the control device 48, for example a microcomputer.

Figure 2:
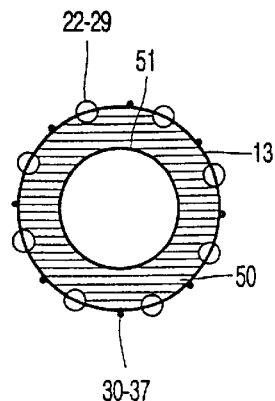
FIG. 2 is a sectional view of a holder containing the calibration medium and the turbid medium.

In order to reconstruct an image of the interior of a part of the turbid medium, for example a part of the breast of a female, during the execution of the intensity measurements the part of the breast to be examined is immersed in a calibration medium present in the holder 13 of the mammography device 1. The calibration medium serves inter alia to couple the light from the measuring light sources into the breast tissue. An example of the calibration medium is an Intralipid solution whose attenuation coefficient $K_1$ corresponds to a predetermined mean attenuation coefficient of the breast tissue. The position of the part of the breast and the calibration medium in the holder will be described in detail with reference to FIG. 2. FIG. 2 is a cross-sectional view of the holder containing the part of the breast of the female and the calibration medium, the shaded part representing the calibration medium present in a space between the holder 13 and the breast 51. Subsequently, the control unit 48 performs intensity measurements for each measuring light source-photodetector pair (i,j), so that an intensity is measured for the shortest light path between the measuring light source i and the photodetector j of the measuring light source-photodetector pair (i,j). The shortest light path is defined as the geometrical distance between the measuring light source i and the photodetector j of the measuring light source-photodetector pair (i,j). Subsequently, the control unit 48 reconstructs an image of the interior of the part of the breast of the female which is situated within the holder 13. Subsequently, a monitor 49 displays the reconstructed image of the interior of the part of the breast. An iterative method which is known from the article "The forward and inverse problems in time resolved infrared imaging", by S. R. Arridge, as published in Medical Optical Tomography, Vol. IS11, 1993, will be described in detail hereinafter with reference to FIG. 3.

Figure 3:
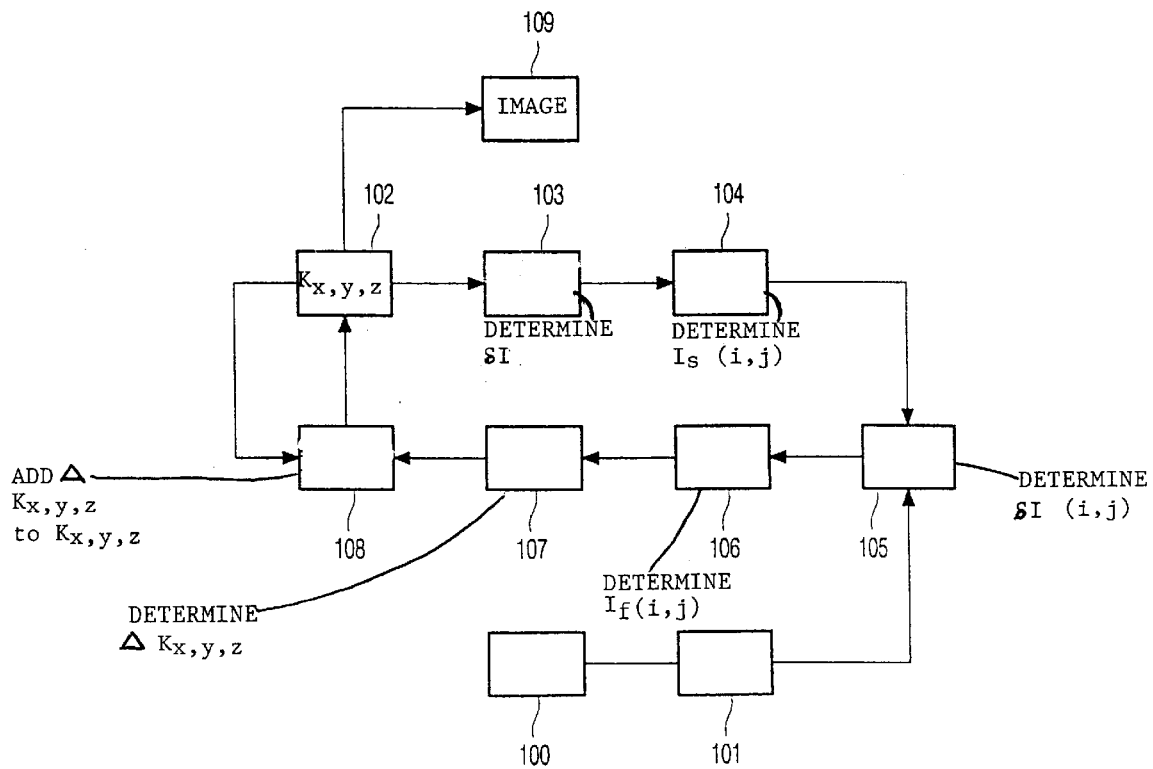
FIG. 3 shows a flow chart of an iterative method for determining an image of a turbid medium.

FIG. 3 shows a flow chart illustrating the known iterative method. During a first step, represented by a first block 100 in FIG. 3, the intensities $I_{i,j}$ of each measuring light source/photodetector pair (i,j) of the holder 13 are measured. During a next step, represented by a second block 101 in FIG. 3, these intensities are stored as a M×N matrix 20 in a memory of the control unit 48. Subsequently, there is chosen an orthogonal system X, Y, Z of voxels which comprises the part of the breast in the holder. With each voxel there is associated an attenuation coefficient $K_{x,y,z}$, which coefficients together constitute a three-dimensional matrix. This is represented by a third block 102 in FIG. 3. During a next step of the method, represented by a fourth block 103 in FIG. 3, a change δI of the estimated intensity $I_s(I,J)$ of the light incident on a photodetector of a measuring light source/photodetector pair I,J of a selected shortest light path is determined from a sum, taken over substantially all voxels present in the part of the breast, of a product of a first function $W_x(x_s,K)$ and a weighting function $W(x_s,\rho,K)$, where K is equal to the product of the attenuation coefficient K and the distance between the measuring light source and a photodetector opening of the selected shortest light path. During a next step, represented by a fifth block 104 in FIG. 3, the estimated intensity associated with the first selected shortest light path is determined and subsequently estimated intensities $I_s(i,j)$ are determined for the plurality of shortest light paths i,j. Subsequently, in a next step of the method, represented by a sixth block 105 in FIG. 3, the differences δI(i,j) are determined for each shortest light path of the measured intensity I(i,j) and the estimated intensity $I_s(i,j)$. From the differences δI(i,j) determined an error estimate $I_f(i,j)$ is determined in a next step which is represented by a seventh block 106 in FIG. 3. Subsequently, a change of the attenuation coefficient $K_{x,y,z}$ of the voxels of the part of the breast is determined in a next step, represented in FIG. 3 by means of an eighth block 107, by way of backprojection of the error estimate. An example of such a backprojection for determining the change of the attenuation coefficient is:

$$\delta K_{x,y,z} = \frac{\sum_{i,j=1}^{i,j=N} I_f(i,j)G(x_s, \rho, K)}{\sum_{i,j=1}^{i,j=N} G(x_s, \rho, K)}$$

where $G(x_s,\rho,K)=W(x_s,\rho,K)$ and $I_f(i,j)$ represents the error estimate between the estimated and the measured intensity of the plurality of shortest light paths. During a next step of the method, represented by a ninth block 108 in FIG. 3, the changes of the attenuation coefficient $K_{x,y,z}$ are added to the values of $K_{x,y,z}$. After some iterations, the values $K_{x,y,z}$ will have been determined sufficiently accurately so as to yield an image of the interior of the part of the breast which is suitable for use for diagnostic purposes. To this end, during a next step of the method, represented by a tenth block 109 in FIG. 3, an image is determined from the three-dimensional matrix of attenuation coefficients $K_{x,y,z}$.

In order to enhance the accuracy of the calculations, the dynamic range of the quantities used in the calculations is limited. To this end, instead of the measured intensity use is preferably made of a normalized intensity I'(i,j) which is determined by the formula:

$$I'(i,j) = \ln\left(\frac{I_{measurement}(i,j)}{I_{cal}(i,j)}\right),$$

in which $I_{measurement}(i,j)$ represents the measured intensity of the measuring light source/detector pair (i,j) in the breast and $I_{cal}(i,j)$ represents a previously measured intensity of the measuring light source/detector pair (i,j) in the holder containing the calibration medium only. Because in practice the actual mean attenuation coefficient $K_2$ of the breast tissue may deviate from the predetermined mean attenuation coefficient $K_1$ of the breast tissue, artifacts could occur in the reconstructed image.

In order to counteract such artefacts, a correction is performed in a version of the method according to the invention. This correction will be described in detail with reference to FIG. 4. The correction is determined by a combination of a normalized intensity of the selected shortest light path, the normalized intensities, lengths of the shortest light paths, and a length of the selected shortest light path. A value of the combination preferably comprises a linear function of the length of the selected light path and a derivative of the normalized intensity to the length of the light path. This linear function can be represented by first reference line along measuring points in a graph, the measuring points corresponding to the plurality of shortest light paths of the measuring light source/detector pairs (i,j), first co-ordinates of said measuring points along a first axis of the graph, being the I' axis, representing the normalized intensities I'(i,j) of the shortest light paths whereas second co-ordinates of said measuring points along a second axis of the graph represent the lengths r(i,j) of the shortest light paths. The normalized intensity is given by $$I'(i,j) = \ln\left(\frac{I_{measurement}(i,j)}{I_{cal}(i,j)}\right)$$

and represents a logarithm of the ratio of the measured intensity $I_{measurement}(i,j)$ of a selected shortest light path i,j of the measuring light source/detector pair (i,j) in the breast and the calibration medium to a predetermined calibration intensity $I_{cal}(i,j)$ associated with the selected shortest light path in the calibration medium. The control unit 48 determines the reference line by means of a linear regression method, for example a least squares method, from the measuring points in the graph. The reference line $1_2$ can subsequently be described by $$\ln\left(\frac{I_{ref}(i,j)}{I_{cal}(i,j)}\right) = a_1 r + b,$$

in which $I_{ref}(i,j)$ and $I_{cal}(i,j)$ represent the intensity of a selected shortest light path in a reference medium and the calibration medium, respectively, $a_1$ represents the direction coefficient of the reference line $1_1$, r represents the length of the selected shortest light path, and b represents a first constant. Using the first constant b, a correction can be made for a change of the coupling-in efficiency and the nature of the change of the attenuation coefficient K. This is intended to mean that the cause of the change of the attenuation coefficient K is a change of the absorption coefficient $\mu_a$ or of the reduced scatter coefficient $\mu_s'$. Thus, if only the absorption coefficient $\mu_a$ varies, the coupling-in efficiency can be compensated by means of a constant b to be selected. If the absorption coefficient $\mu_a$ varies as well as the reduced scatter coefficient $\mu_s'$, the coupling-in efficiency as well as the change of the reduced scatter coefficient $\mu_s'$ can be compensated by means of the constant b. The first constant b is determined by the distance between a point of intersection of the reference line $1_2$ and the I' axis of the graph relative to an origin of the graph. The corrected intensity I"(i,j) for a shortest light path $r_{i,j}$ of a measuring light source/detector pair (i,j) is determined by $$I''(i, j) = \ln\left(\frac{I_{measurement}(i, j)}{I_{ref}(i, j)}\right) = \ln\left(\frac{I_{measurement}(i, j)}{I_{cal}(i, j)}\right) - a_1 r(i, j) - b,$$

where r(i,j) represents the shortest light path between the measuring light source i and the detector j, $a_1$ represents the direction coefficient determined, and b represents the first constant. The corrected intensity I"(i,j) then approximates a measured intensity relative to the reference medium whose attenuation coefficient equals the actual mean attenuation coefficient $K_2$ of the part of the breast. Subsequently, a reconstruction is performed in conformity with the description given with reference to FIG. 3. This yields a three-dimensional matrix of the attenuation coefficients $K_{x,y,z}$ relative to the reference medium. The control unit 48 subsequently determines the reconstructed image by selecting attenuation coefficients from the three-dimensional matrix $K_{x,y,z}$ which correspond to voxels in the breast which are situated in one plane. The reconstructed image can be corrected for the calibration medium used by adding a second constant to attenuation coefficients of voxels of the turbid medium which correspond to pixels of the reconstructed image, the second constant being equal to the direction coefficient $a_1$ determined which corresponds to the difference $K_2-K_1$ between the attenuation coefficient of the reference medium and the attenuation coefficient of the calibration medium.

Figure 4:
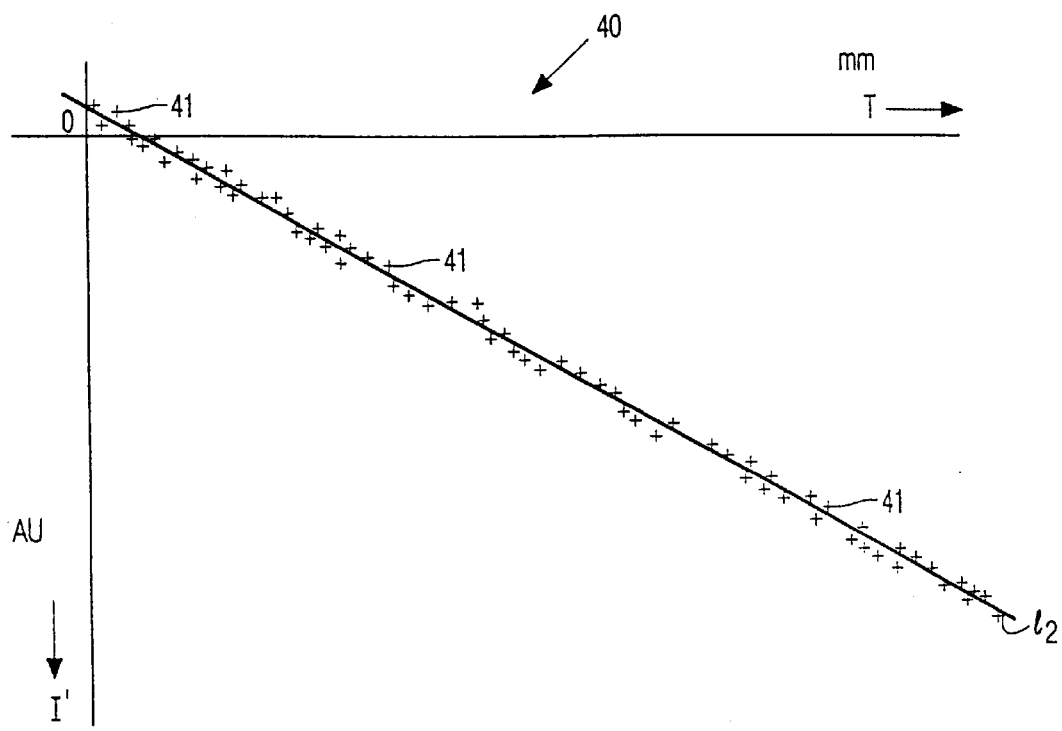
FIG. 4 shows a graph in which the normalized intensity I' is given as a function of the shortest length between the source and the detector.

The determination of the direction coefficient $a_1$ will be described in detail with reference to FIG. 4. FIG. 4 shows a graph 40 of reference measuring points 41 which have been obtained by successive measurements, using the device 1, of intensities of the measuring light source/detector pairs (i,j) in the holder 13 containing a reference medium, for example a liquid having an attenuation coefficient $K_2$. The holder 13 also has a reflective inner wall which has a reflection coefficient of, for example 70%. A co-ordinate of a reference measuring point 41 along an I' axis of the graph 40 represents the normalized intensity relative to the calibration medium which is given by the logarithm of the ratio of the measured intensity $I_{ref}(i,j)$ of a selected shortest light path i,j from a reference measuring point associated with the measuring light source/detector pair (i,j) in the reference medium to a previously measured intensity $I_{cal}(i,j)$ associated with the selected shortest light path in the calibration medium. A co-ordinate of the reference measuring point 41 along an r axis of the graph 40 represents a length of the selected shortest light path r(i,j) associated with the measuring light source/detector pair (i,j) corresponding to the reference measuring point. The graph shows that for a uniform reference medium, having an attenuation coefficient $K_2$, the reference measuring points are situated substantially on the reference line $1_2$ whose direction coefficient $a_1$ corresponds to the difference $K_2-K_1$ between the attenuation coefficient of the reference medium and that of the calibration medium, respectively. The first constant b corresponds to the distance between a point of intersection of the reference line $1_2$ with the I' axis relative to the origin of the graph 40.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of localizing an object in a turbid medium, comprising:

immersing the turbid medium in a calibration medium, irradiating the turbid medium, measuring intensities of a part of light transported through the turbid medium and the calibration medium along a plurality of light paths, normalizing the measured intensities, performing a correction on the normalized intensities to realize corrected normalized intensities by generating a corrected normalized intensity of each selected light path including combining a normalized intensity of a selected light path, the normalized intensities, lengths of the light paths, and a length of the selected light path, and reconstructing an image of the interior of the turbid medium utilizing the corrected normalized intensities.

2. A method as claimed in claim 1 wherein the value of the combination comprises a function of the length of the selected light path and a derivative of the normalized intensity to the length of the light path.

3. A method as claimed in claim 2, characterized in that the value of the combination contains a first constant which is determined by a distance between a point of intersection of a reference line and a first axis of a graph relative to an origin of the graph, the reference line representing a logarithm of a ratio of a measured intensity of the calibration medium to a measured intensity of a reference medium.

4. The method of claim 2 wherein the normalized intensity of a light path to be selected is determined by a logarithm of a ratio of a first intensity of a selected light path in the turbid medium and the calibration medium to a second intensity of the selected light path in the calibration medium.

5. The method of claim 4 wherein the reconstructed image is corrected for the calibration medium by adding a constant to attenuation coefficients of voxels of the turbid medium, which voxels correspond to pixels of the reconstructed image.

6. The method of claim 2 wherein the reconstructed image is corrected for the calibration medium by adding a constant to attenuation coefficients of voxels of the turbid medium, which voxels correspond to pixels of the reconstructed image.

7. A method as claimed in claim 1 wherein the normalized intensity of a light path to be selected is determined by a logarithm of a ratio of a first intensity of a selected light path in the turbid medium and the calibration medium to a second intensity of the selected light path in the calibration medium.

8. The method of claim 7 wherein the reconstructed image is corrected for the calibration medium by adding a constant to attenuation coefficients of voxels of the turbid medium, which voxels correspond to pixels of the reconstructed image.

9. A method as claimed in claim 1 wherein the reconstructed image is corrected for the calibration medium by adding a second constant to attenuation coefficients of voxels of the turbid medium, which voxels correspond to pixels of the reconstructed image.

10. A device for the imaging of objects in a turbid medium comprising:

- a holder for receiving a calibration medium and for receiving the turbid medium,
- a light source for irradiating the turbid medium and the calibration medium,
- means for coupling the light to be generated by the light source into the turbid medium from different angles,
- a plurality of photodetectors for measuring the light transported through the turbid medium and the calibration medium in different directions,
- means for selecting a photodetector from among the plurality of photodetectors,
- a control device for generating control signals for the means for coupling the light into at least one of the calibration medium and the turbid medium from different light paths and for selecting one of the photodetectors,
- means for normalizing measured intensities of each light path, to provide normalized intensities,
- a control unit for reconstructing an image of the interior of the turbid medium, and
- correction means for performing a correction on each of the normalized intensities corresponding to each light path to generate corrected normalized intensities, wherein each corrected normalized intensity of each light path selected is determined by a combining a normalized intensity of the selected light path, the normalized intensities, lengths of the light paths, and a length of the selected light path, wherein said control unit utilizes the corrected normalized intensities to reconstruct said image.

* * * * *